(12) United States Patent
Oosterhoff et al.

(10) Patent No.: US 7,957,801 B2
(45) Date of Patent: Jun. 7, 2011

(54) DYNAMIC PACING INTERVAL EXTENSION FOR DETECTION OF INTRINSIC VENTRICULAR ACTIVITY

(75) Inventors: Peter Oosterhoff, Zutphen (NL); Henricus W. M. De Bruyn, Arnhem (NL)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 10/822,487

(22) Filed: Apr. 12, 2004

(65) Prior Publication Data

US 2005/0010255 A1 Jan. 13, 2005

Related U.S. Application Data

(63) Continuation-in-part of application No. 10/424,585, filed on Apr. 25, 2003, now abandoned.

(51) Int. Cl.
*A61N 1/365* (2006.01)
(52) U.S. Cl. ............................. 607/17; 607/25
(58) Field of Classification Search .............. 607/14, 607/17, 25
See application file for complete search history.

(56) References Cited

U.S. PATENT DOCUMENTS

| | | | |
|---|---|---|---|
| 5,470,344 A * | 11/1995 | Begemann | 607/17 |
| 5,716,383 A | 2/1998 | Kieval et al. | |
| 5,861,007 A | 1/1999 | Hess et al. | |
| 6,269,268 B1 * | 7/2001 | Callaghan et al. | 607/26 |
| 6,285,907 B1 * | 9/2001 | Kramer et al. | 607/9 |
| 6,498,950 B1 | 12/2002 | Bradley | |
| 6,836,682 B2 * | 12/2004 | Van Dam | 607/25 |
| 2003/0050671 A1 * | 3/2003 | Bradley | 607/27 |
| 2003/0153954 A1 * | 8/2003 | Park et al. | 607/17 |
| 2004/0215277 A1 | 10/2004 | Oosterhoff | |

FOREIGN PATENT DOCUMENTS

| | | |
|---|---|---|
| EP | 0836867 | 4/1998 |
| WO | 0137927 | 5/2001 |

OTHER PUBLICATIONS

International Search Report, PCT/US2004/011726, Oct. 6, 2004.
International Search Report, PCT/US2005/011854, Jul. 19, 2005.

* cited by examiner

*Primary Examiner* — Carl H. Layno
*Assistant Examiner* — Tammie K Heller
(74) *Attorney, Agent, or Firm* — Stepehn W. Bauer; Reed A. Duthler (57) ABSTRACT

Methods and devices for identification of intrinsic ventricular activity occurring within a ventricular signal. Ventricular signal morphology is analyzed to determine if the signal contains intrinsic ventricular activity while delivering pacing pulses separated by nearly constant time intervals. Furthermore, an extension of a pacing interval is specified based on whether or not the signal contains autonomous intrinsic ventricular activity. In this manner, the pacing interval is only extended when it is likely for autonomous intrinsic ventricular activity to occur.

20 Claims, 8 Drawing Sheets

DYNAMIC PACING INTERVAL EXTENSION FOR DETECTION OF INTRINSIC VENTRICULAR ACTIVITY

RELATED APPLICATION

This application is a continuation-in-part of U.S. patent application Ser. No. 10/424,585 filed on Apr. 25, 2003, now abandoned, entitled "DYNAMIC PACING INTERVAL EXTENSION FOR DETECTION OF INTRINSIC VENTRICULAR ACTIVITY", to Oosterhoff, incorporated herein by reference in its entirety.

FIELD OF THE INVENTION

The invention relates to implantable medical devices and, more particularly, to cardiac pacemakers that extend a pacing interval on detection of intrinsic activity.

BACKGROUND OF THE INVENTION

Many patients suffer from the occurrence of a heart block, in which an electrical signal propagating from the sinoatrial node is stopped at the atrioventricular valve or just below the atrioventricular node. The heart block effectively blocks the electrical signal from reaching the ventricles and causing them to contract. In some situations, the heart block may not fully obstruct the electrical signal from propagating to the ventricles. In these instances, conduction may be slowed, or may be of intermittent nature. Implantable medical devices (IMDs), such as pacemakers, may detect the intrinsic ventricular activity via electrodes placed within or around the heart.

When the heart block succeeds in fully blocking the electrical signal from reaching the ventricles, a pacemaker detects the absence of intrinsic electrical activity in the heart and applies a pacing pulse to stimulate the ventricles to contract. Pacemakers use various algorithms to determine when to apply a pacing pulse. Ideally, a pacemaker should only apply a pacing pulse when intrinsic ventricular activity does not occur within the heart.

This strategy is ideal because hemodynamic performance and the battery life of the pacemaker are increased when intrinsic ventricular activity occurs as opposed to the delivery of a pacing by the pacemaker delivering a pacing pulse to stimulate the ventricles. Thus, it is beneficial to detect the presence of intrinsic ventricular activity.

Intrinsic ventricular activity following a pace is understood to be either fusion or pseudo fusion. In the case of pseudofusion, the pacemaker fails to detect a depolarization and a stimulus is delivered during or after the intrinsic depolarization, but it has no capture because the cardiac tissue is already refractory, there is a ventricular sense, or a pace was given while the heart was contracting due to a natural trigger.

Pacemakers may determine occurrence of intrinsic ventricular activity by extending a pacing interval between a delivered pacing pulse and a subsequently delivered pacing pulse. This process is sometimes referred to as hysteresis. The pacemaker generally schedules the extended pacing interval to occur once per time-unit or once per number of cycles. During the scheduled extended pacing interval, the pacemaker monitors the heart for intrinsic ventricular activity. In the event that intrinsic ventricular activity occurs is detected, the pacemaker does not apply a pacing to the ventricle of the heart. Otherwise, at the end of the extended pacing interval, the pacemaker delivers a pacing pulse to stimulate contraction of the ventricle.

One of the advances provided by utilizing the present invention rather than a common scan method to detect intrinsic activity is that no symptomatic large interval extension is needed, while the chance of detecting intrinsic activity is significantly larger than when using a (non-symptomatic) small interval extension.

BRIEF SUMMARY OF THE INVENTION

In general, the invention is directed to identification of intrinsic ventricular activity occurring within a ventricular signal following delivery of a pacing pulse to the ventricle by an IMD. In particular, the IMD analyzes one or more morphological characteristics associated with the ventricular signal to determine if the post-pacing ventricular signal contains an indication of possible intrinsic ventricular activity. The IMD extends the next pacing interval when the ventricular signal contains an indication of possible intrinsic ventricular activity. The IMD delivers pacing pulses at substantially fixed pacing intervals, provided there is no indication of intrinsic ventricular activity. Once intrinsic ventricular activity is detected, the IMD extend the next pacing interval to allow intrinsic ventricular activity. In this manner, the IMD can detect intrinsic ventricular activity and avoid delivery of unnecessary pacing pulses without the need for periodic extension of the pacing interval, i.e., hysteresis. Instead, the IMD dynamically extends the pacing interval in response to an indication of possible intrinsic ventricular activity.

In general, the IMD stores a set of morphology criteria in the form of a template. The template can be either static or dynamic. A static template can be generated during a training period, in which the implanted medical device detects numerous ventricular signals and stores morphology information relating to ventricular signals, which fully capture a ventricle of a heart. A dynamic template can be generated upon enabling the device and is continuously updated with morphology information pertaining to the most recent ventricular signal. In both cases, past ventricular signals and their associated morphology criteria form the basis of the templates, which are used to compare against subsequent ventricular signals. Notably, the criteria may be unique for each individual patient. In this manner, the templates may reflect the particular physical condition, disease state, and activity profile of the patient.

In response to the comparison of the sensed ventricular signal to the template, the implanted medical device determines whether to extend a pacing interval between the delivered pacing pulse and a subsequent pacing pulse. In each case, the implanted medical device can distinguish many ventricular signals that contain intrinsic ventricular activity, and thereby extend the pacing interval allowing the intrinsic ventricular activity to occur undisturbed. If the intrinsic ventricular activity does occur during the extended pacing interval, then the implanted medical device does not need to deliver a pacing pulse thereby reducing the number of pacing pulses delivered to the patient, and the associated consumption of battery resources. Accordingly, the invention can be helpful in accurately extending a pacing interval only when necessary, which improves hemodynamic flow of the heart and increases patient comfort.

In one embodiment, the invention is directed to a method comprising delivering a pacing pulse to a heart, detecting intrinsic ventricular activity within the heart after delivering the pacing pulse, and extending a pacing interval between the delivered pacing pulse and a subsequently delivered pacing pulse based on the detection of intrinsic ventricular activity.

In another embodiment, the invention provides a device comprising at least one electrode to deliver a pacing pulse to a heart, and a processor that detects intrinsic ventricular activity within the heart after delivering the pacing pulse and extends a pacing interval between the delivered pacing pulse and a subsequently delivered pacing pulse based on the detection of intrinsic ventricular activity.

In a further embodiment, the invention provides a computer-readable medium comprising instructions to cause a processor to control a pulse generator to deliver a pacing pulse to a heart, detect intrinsic ventricular activity within the heart after delivering the pacing pulse, and extend a pacing interval between the delivered pacing pulse and a subsequently delivered pacing pulse based on the detection of intrinsic ventricular activity.

The details of one or more embodiments of the invention are set forth in the accompanying drawings and the description below. Other features, objects, and advantages of the invention will be apparent from the description and drawings, and from the claims.

DETAILED DESCRIPTION OF THE INVENTION

Figure 1:
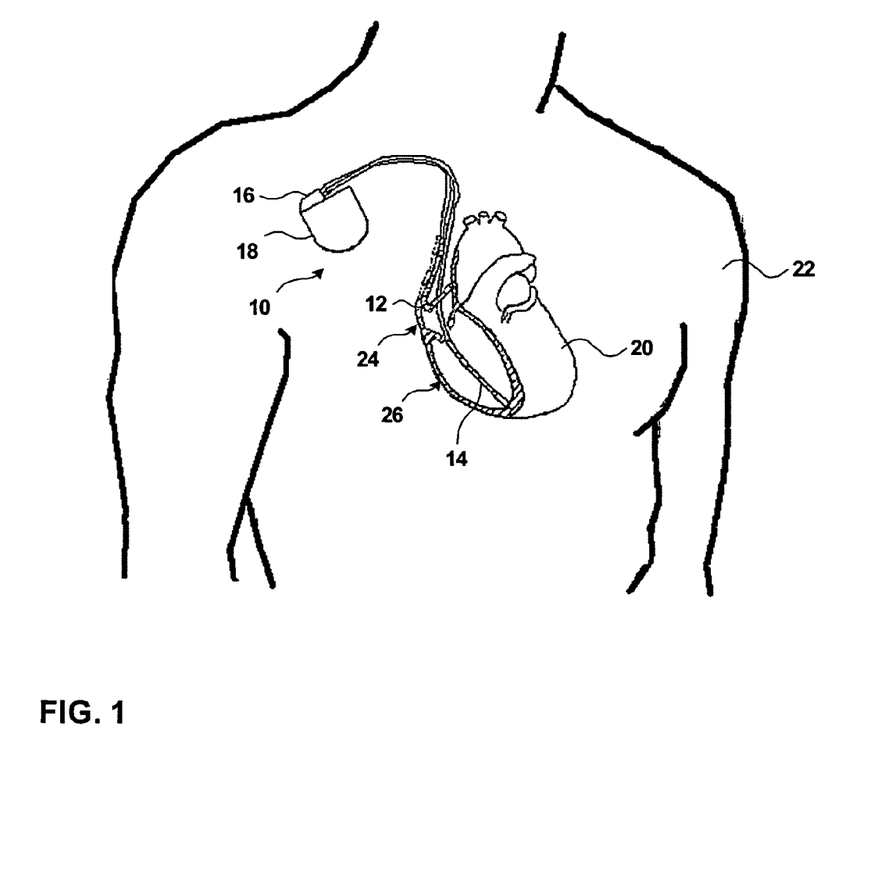
FIG. 1 is a schematic view of an exemplary implantable medical device implanted within a human body.

FIG. 1 is a schematic view of an exemplary implantable medical device 10 implanted within a human patient 22. For purposes of illustration, this disclosure refers extensively to the detection and identification of intrinsic ventricular activity. In some embodiments, however, the invention may be applicable to detection of intrinsic atrial activity. Accordingly, description of detection of intrinsic ventricular activity this disclosure should not be considered limiting of the invention as broadly claimed and embodied herein.

IMD 10 identifies intrinsic ventricular activity occurring within heart 20 of patient 22. In particular, IMD 10 is capable of distinguishing ventricular signals without intrinsic ventricular activity from ventricular signals containing intrinsic ventricular activity by analyzing the signal directly after a pace pulse is delivered pulses to heart 20. The pacing pulses may be delivered at nearly constant intervals, without the need for periodic extension of the pacing interval, i.e., hysteresis. Instead, IMD 10 dynamically responds to identification of possible intrinsic ventricular activity following delivery of a pacing pulse by extending the next pacing interval to verify presence of intrinsic ventricular activity.

As will be described, IMD 10 analyzes the morphology associated with a ventricular signal sensed following the delivery of a pacing pulse to the ventricle. In particular, IMD 10 analyzes the morphology of the sensed signal relative to morphology criteria indicative of the possible presence of intrinsic ventricular activity. The morphology criteria may be associated with previous ventricular signals known to contain intrinsic ventricular activity, or with previous ventricular signals known to lack intrinsic ventricular activity, and can be represented by a morphology template specifying a number of morphological parameter values.

By comparing morphological characteristics of the sensed ventricular signal to the morphology template, IMD 10 determines whether intrinsic ventricular activity may be occurring. Notably, IMD 10 identifies intrinsic ventricular activity even though the sensed ventricular signal follows delivery of a pacing pulse. In this sense, IMD 10 detects the intrinsic ventricular activity within a paced ventricular response. In response to the comparison, IMD 10 determines whether to extend the pacing interval between the delivered pacing pulse and a subsequently delivered pacing pulse to allow intrinsic ventricular activity. If intrinsic ventricular activity is detected, IMD 10 keeps using the extended interval, thus permitting the intrinsic ventricular activity to occur. In this manner, IMD 10 can improve hemodynamic performance and avoid unnecessary delivery of pacing pulses, thereby increasing device longevity.

In the example of FIG. 1, IMD 10 is a pacemaker comprising atrial pacing and sensing lead 12 and ventricular pacing and sensing lead 14 attached to connector module 16 of hermetically sealed enclosure 18 and implanted near human or mammalian heart 20 of patient 22. Pacing and sensing leads 12 and 14 sense electrical signals attendant to the depolarization and repolarization of the heart 20, and further provide pacing pulses for causing depolarization of cardiac tissue in the vicinity of the distal ends thereof. Leads 12 and 14 may have unipolar or bipolar electrodes disposed thereon.

IMD 10 is one example of a device capable of practicing the invention, in that IMD 10 has the capability of delivering a pacing pulse to a heart, detecting intrinsic ventricular activity within the heart, and extending a pacing interval between the delivered pacing pulse and a subsequent pacing pulse based on the detection of intrinsic ventricular activity. In particular, ventricular pacing and sensing lead 14 delivers a pacing pulse to right ventricle 26 and senses a ventricular signal resulting from the delivery of the pacing pulse. IMD 10 processes the ventricular signal and determines if the signal contains intrinsic ventricular activity. If IMD 10 determines the ventricular signal contains intrinsic ventricular activity then the pacing interval is extended. However, if the signal does not contain intrinsic ventricular activity, IMD 10 continues to deliver pacing pulses separated by nearly constant time intervals.

Atrial pacing and sensing lead 12 senses activation of the right atrium 24, and can pace right atrium 26. IMD 10 is not the only implantable medical device that may practice the invention, however. The invention, alternatively, can be practiced by implantable medical devices that are configured to pace one, three or four chambers of heart 20, and may further be applicable for implementation in cooperation with single chamber devices, both atrial and ventricular.

Figure 2:
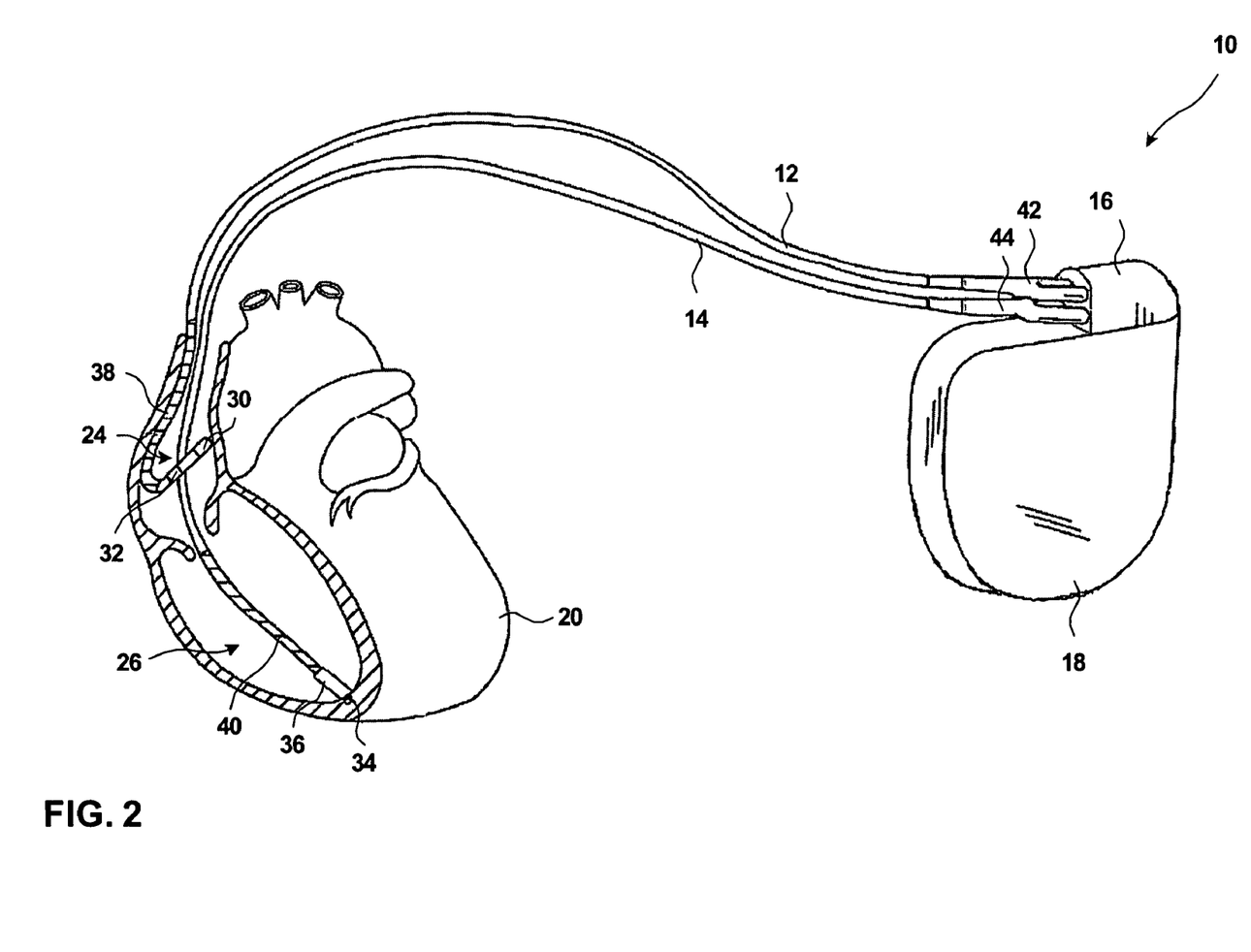
FIG. 2 is a diagram of the implantable medical device of FIG. 1 located in and near a heart.

FIG. 2 is a diagram of implantable medical device 10 of FIG. 1 located in and near heart 20. FIG. 2 shows IMD 10, with connector module 16 and hermetically sealed enclosure 18. Atrial and ventricular pacing leads 12 and 14 extend from connector module 16 to the right atrium 24 and right ventricle 26, respectively, of heart 20.

Atrial electrodes 30 and 32 disposed at the distal end of atrial pacing lead 12 are located in right atrium 24. Ventricular electrodes 34 and 36 disposed at the distal end of ventricular pacing lead 14 are located in right ventricle 26.

A pulse generator (not shown in FIG. 2) inside enclosure 18 generates pacing pulses. The pacing pulses are delivered to right atrium 24 or right ventricle 26 by electrodes 30, 32, 34, 36. In accordance with the invention, a pacing pulse is delivered to right ventricle 26 and a ventricle signal in response to the ventricular pulse is monitored by lead 14. A processor (not shown in FIG. 2) in IMD 10 determines if the ventricular signal contains intrinsic ventricular activity, and if so the processor responds by extending a pacing interval between the delivered pacing pulse and a subsequent pacing pulse. By extending the pacing interval, the processor effectively allows intrinsic ventricular activity to occur undisturbed by the subsequent pacing pulse, which eliminates the need to deliver a ventricular pace and as a result increases patient comfort, lengthens battery life and improves hemodynamic function within heart 20. If the processor does not detect intrinsic ventricular for a single or multi consecutive beats, the extension of the pacing interval can be disabled.

In addition to pacing, IMD 10 can apply other forms of therapy. In FIG. 2, for example, atrial lead 12 and ventricular lead 14 include defibrillation electrodes 38 and 40, respectively. Defibrillation electrodes 38 and 40 deliver defibrillation shocks to right atrium 24 or right ventricle 26 when necessary to terminate an episode of atrial or ventricular defibrillation. Atrial and ventricular leads 12, 14 each include an elongated insulative lead body carrying one or more conductors insulatively separated from one another. At the proximal end of leads 12, 14 are bifurcated connectors 42, 44, which electrically couple the connectors to connector module 16 of IMD 10.

Figure 3:
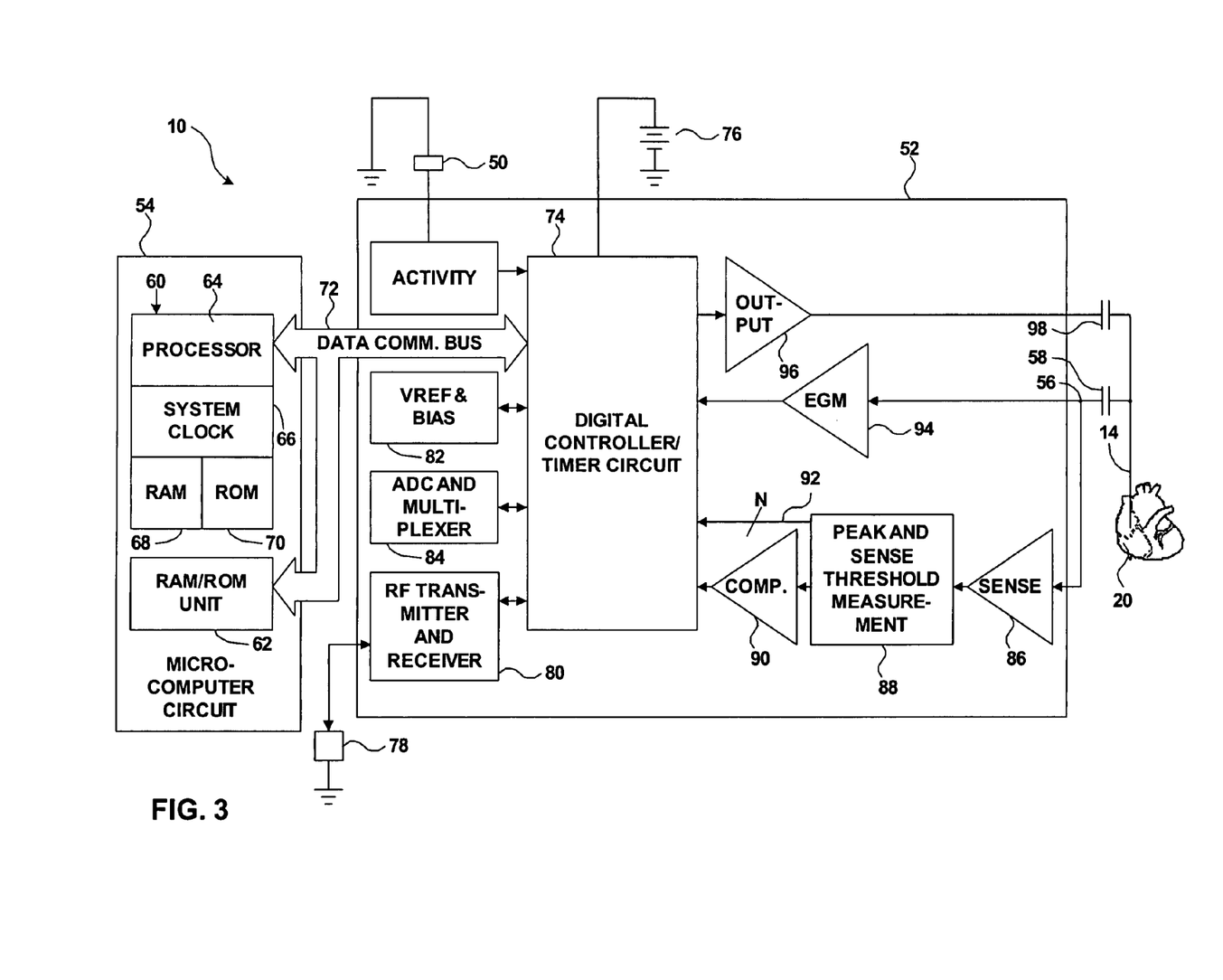
FIG. 3 is a block diagram illustrating the constituent components of the implantable medical device depicted in FIGS. 1 and 2.

FIG. 3 shows a block diagram illustrating exemplary components of IMD 10 in accordance with one embodiment of the invention, in which IMD 10 is a pacemaker having a microprocessor-based architecture. As shown in FIG. 3, IMD 10 can include one or more activity sensors 50. Activity sensor 50 may include an accelerometer, such as a piezoceramic accelerometer or a microelectromechanical accelerometer, that provides a sensor output that varies as a function of a measured parameter relating to a patient's metabolic requirements. In other words, activity sensor 50 detects motion of patient 22 that accompanies physical activity, and may adjust a pacing rate to the metabolic needs associated with the physical activity.

The output of activity sensor 50 is coupled to input/output circuit 52. Input/output circuit 52 contains analog circuits for interfacing with heart 20, activity sensor 50, and other components and circuits for the application of stimulating pulses to heart 20. For ease of illustration, IMD 10 in FIG. 3 is shown with only lead 14 connected. Similar circuitry and connections not explicitly shown in FIG. 3 apply to lead 12 (shown in FIGS. 1 and 2), however. Lead 14 is coupled to node 56 in IMD 10 through input capacitor 58.

The rate of heart 20 is controlled by software-implemented algorithms stored within microcomputer circuit 54. In the example of FIG. 3, microcomputer circuit 54 comprises on-board circuit 60 and off-board circuit 62. On-board circuit 60 may include processor 64, system clock circuit 66 and on-board random access memory (RAM) 68 and read-only memory (ROM) 70. Processor 64 may take the form of a microprocessor, digital signal processor (DSP), ASIC, FPGA, or other integrated or discrete logic circuitry capable of performing the functions described herein. Off-board circuit 62 comprises a RAM/ROM unit. On-board circuit 60 and off-board circuit 62 are each coupled by data communication bus 72 to digital controller/timer circuit 74. Microcomputer circuit 54 may comprise a custom integrated circuit device augmented by standard RAM/ROM components.

Microcomputer circuit 54 extends a pacing interval by extending the delivery of a subsequent ventricular pacing pulse in response to a detected intrinsic ventricular activity, which allows the intrinsic ventricular activity to occur undisturbed. If the intrinsic ventricular activity occurs during the extended pacing interval then a ventricular pacing pulse is not delivered which conserves battery power while improving hemodynamic performance and patient comfort. In accordance with the invention, IMD 10 detects intrinsic ventricular activity within a ventricular signal, and determines whether to extend the pacing interval. In particular, IMD 10 is configured to identify intrinsic ventricular activity within a ventricular signal while delivering pacing pulses to heart 20, which are separated by nearly constant intervals. If IMD 10 determines that intrinsic ventricular activity did not occur, IMD 10 does not extend the pacing interval and continues to deliver pacing pulses separated by nearly constant time intervals. If intrinsic ventricular activity is detected within a ventricular signal, however, IMD 10 extends the pacing interval by delaying delivery of a subsequent ventricular pacing pulse via lead 14.

Processor 64 of IMD 10 analyzes the detected ventricular signal to determine whether the ventricular signal contains intrinsic ventricular activity. For example, processor 64 can compare one or more morphological characteristic, such as the minimum amplitude of the detected ventricular signal, with the same morphological characteristics of a past ventricular signal to classify the detected ventricular signal as containing or not containing an occurrence of intrinsic ventricular activity based on the comparison of the morphological characteristics. In some instances, templates generated during training phases represent the past ventricular signals. If the morphological characteristic comparison falls in a range that is indicative of an occurrence of intrinsic ventricular activity, processor 64 controls digital controller/timer circuit 74 to delay delivery of the subsequent pacing pulse which extends the pacing interval. In some embodiments, a dedicated detector circuit, either integrated or discrete, may be provided to perform the function of identifying ventricular signals containing intrinsic ventricular activity based on morphology. Processor 64 may be more desirable, however, in terms of processing power and programming flexibility.

In general, microcomputer circuit 54 stores a set of morphology criteria in the form of a template that aid in distinguishing ventricular signals that exhibit intrinsic ventricular activity from ventricular signals that do not. The criteria can comprise thresholds, which define a limit for acceptable variation of a current ventricular signal from a past ventricular signal. Further criteria can specify how many morphology characteristics are used in the comparison as well as how many thresholds that can be exceeded before a signal is classified as containing an occurrence of intrinsic ventricular activity.

The criteria may be developed during the course of a training period in which the IMD 10 detects numerous ventricular signals containing intrinsic ventricular activity and stores information relating to the morphologies associated with the ventricular signals containing intrinsic ventricular activity. Based on the training period, IMD 10 develops the criteria for comparison to subsequently detected ventricular signals, which can contain intrinsic ventricular activity, to identify ventricular signals that actually contain intrinsic ventricular activity. IMD 10 performs the training period following implant and, consequently, the criteria may be unique for each individual patient 11. In this manner, the criteria may reflect the particular physical condition, disease state, and activity profile of the patient 11. Templates can incorporate these criteria to account for differences between individual patients.

In operation, following the training period, IMD 10 detects ventricular signals that contain intrinsic ventricular activity and identifies morphology characteristics of the ventricular signals. IMD 10 then compares the characteristics to templates obtained from the training period, generated during operation of IMD 10 or both. In response to the comparison, IMD 10 determines whether to extend the pacing interval. As a result, IMD 10 can distinguish many ventricular signals that contain intrinsic ventricular activity, extend the pacing interval, thereby allowing the intrinsic ventricular activity to occur undisturbed and avoiding unnecessary delivery of ventricular pacing pulses.

Electrical components shown in FIG. 3 are powered by an appropriate implantable battery power source 76. For ease of illustration, the coupling of battery power to the various components of IMD 10 is not shown in FIG. 3. IMD 10 reduces the number of ventricular pacing pulses delivered to the patient by allowing intrinsic ventricular activity to occur undisturbed, and the associated consumption of battery resources provided by batter power source 76. Accordingly, IMD 10 can be effective in avoiding unnecessary therapies and increasing device longevity.

Antenna 78 is connected to input/output circuit 52 to permit uplink/downlink telemetry through radio frequency (RF) transmitter and receiver telemetry unit 80. IMD 10 in FIG. 3 is programmable by an external programmer (not shown) that communicates with IMD 10 via antenna 78 and RF transmitter and receiver telemetry unit 80.

In some embodiments, an external programming unit can be used to cause IMD 10 to enter into a training period in which the IMD detects numerous ventricular signals containing intrinsic ventricular activity and stores characteristics for the signals, such as morphology characteristics. At the end of the training period, or during the course of the training period, IMD 10 processes the stored characteristics to generate one or more templates. The templates incorporate past ventricular signals and accompanying criteria that specify ranges of ventricular signal morphological characteristics observed to indicate that the ventricular signal contains intrinsic ventricular activity.

VREF and Bias circuit 82 generates stable voltage reference and bias currents for analog circuits included in input/output circuit 52. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of IMD 10 are transmitted from processor 64 via data bus 72 to digital controller/timer circuit 74, where digital timers and counters establish the overall escape interval of the IMD 10 as well as various refractory, blanking and other timing windows for controlling the operation of peripheral components disposed within input/output circuit 52.

Digital controller/timer circuit 74 is coupled to sensing circuitry, including sense amplifier 86, peak sense and threshold measurement unit 88 and comparator/threshold detector 90. Sense amplifier 86 amplifies electrical cardiac signals sensed via lead 14 and provides an amplified signal to peak sense and threshold measurement circuitry 88, which in turn provides an indication of peak sensed voltages and measured sense amplifier threshold voltages on multiple conductor signal path 92 to digital controller/timer circuit 74. An amplified sense amplifier signal is also provided to comparator/threshold detector 90.

Digital controller/timer circuit 74 is further coupled to electrogram (EGM) amplifier 94 for receiving amplified and processed signals sensed by lead 14. The electrogram signal provided by EGM amplifier 94 is employed, for example, as input for the analysis of the ventricular or atrial signals after a ventricular or atrial pace, to determine whether or not intrinsic activity is present in that signal. Output pulse generator 96 provides pacing stimuli to heart 20 through coupling capacitor 98 in response to a pacing trigger signal provided by digital controller/timer circuit 74.

IMD 10 can sense P-waves, i.e., atrial depolarizations, and R-waves, i.e. ventricular depolarizations or ventricular signals, via lead 12 and lead 14, respectively. The signals then propagate through sense amplifier 86, peak sense and threshold measurement unit 88 and comparator/threshold detector 90. IMD 10 further delivers pacing pulses to the atrium and ventricle via leads 12 and 14, respectively. In this manner, the atrium to ventricular (AN) time interval between a P-wave and a subsequent R-wave can be extended by delaying the delivery of a ventricular pulse which causes the depolarization of the ventricle.

Sense amplifier 86, peak sense and threshold measurement unit 88 and comparator/threshold detector 90 are configured to serve as part of an intrinsic ventricular activity detector. In response to intrinsic ventricular activity detection within a ventricular signal, processor 64 directs digital controller/timer circuit 74 to extend the AN or VN interval by delaying delivery of the ventricular pacing pulse.

In general, IMD 10 analyzes one or more morphology characteristics of the detected ventricular signals to identify ventricular signals that contain intrinsic ventricular activity. Examples of morphology characteristics that may used to distinguish ventricular signals containing intrinsic ventricular activity include any of the following: minimum voltage of the ventricular signal, maximum voltage of the ventricular signal, time of maximum voltage from the start of the ventricular signal, time of minimum voltage of the ventricular signal, maximum slope of the ventricular signal, time of maximum slope of the ventricular signal from the start of the ventricular signal, minimum slope of the ventricular signal, time of minimum slope of the ventricular signal from the start of the ventricular signal, T-wave timing, T-wave amplitude, and ventricular signal width, i.e., time between first and last amplitude threshold crossings of the ventricular signal. Each of the above morphology characteristics may be analyzed within a filtered or unfiltered signal representing the detected ventricular signal. Such morphology characteristics may be efficiently processed, identified and compared using digital signal analysis. In this case, processor 64 may take the form of a digital signal processor (DSP), or IMD 10 may further include a DSP.

One or more of the above morphology characteristics may be observed as a characteristic of a ventricular signal that is more likely to contain an occurrence of intrinsic ventricular activity. The significance of the individual characteristics, as well as the effect of the particular value ranges of the characteristics can vary from patient-to-patient. Accordingly, IMD 10 can be configured to establish unique ranges for the characteristics as a result of a training period. In the training period, IMD 10 detects numerous ventricular signal containing intrinsic ventricular activity and processes and stores morphological characteristics for the signals containing intrinsic ventricular activity, such as minimum and maximum voltage, slope, and the like. On the basis of the stored data, IMD 10 generates morphology characteristic criteria, such as thresholds or ranges, to distinguish ventricular signals containing an occurrence of intrinsic ventricular activity from ventricular signals that do not contain an occurrence of intrinsic ventricular activity, and stores the criteria in the form of a template. IMD 10 thereafter compares one or more morphology characteristics of newly detected ventricular signals to the template to determine whether the newly detected ventricular signals contain an occurrence of intrinsic ventricular activity. If so, IMD 10 extends the AN or VN time interval by delaying delivery of a subsequent ventricular pulse pace. If the detected ventricular signal does not contain an occurrence of intrinsic ventricular activity, IMD 10 continues to deliver ventricular pacing pulses to maintain a previous VN or AN time interval.

As described herein, IMD 10 may identify intrinsic ventricular activity within a ventricular signal based on one or more morphology characteristics associated with the ventricular signal and intrinsic ventricular activity. IMD 10 can identify intrinsic ventricular activity by comparing morphology characteristics using templates generated from a past ventricular signal representative of a ventricular signal where the heart is fully captured or a most recent ventricular signal. Furthermore, IMD 10 can modulate the AN or VN interval slightly and compare one or more morphology characteristics using criteria generated as above, such as a most recent ventricular signal. In some embodiments, however, IMD 10 can utilize one or more of the above techniques simultaneously to identify ventricular signals containing an occurrence of intrinsic ventricular activity and is not limited to using a single technique.

Figure 4:
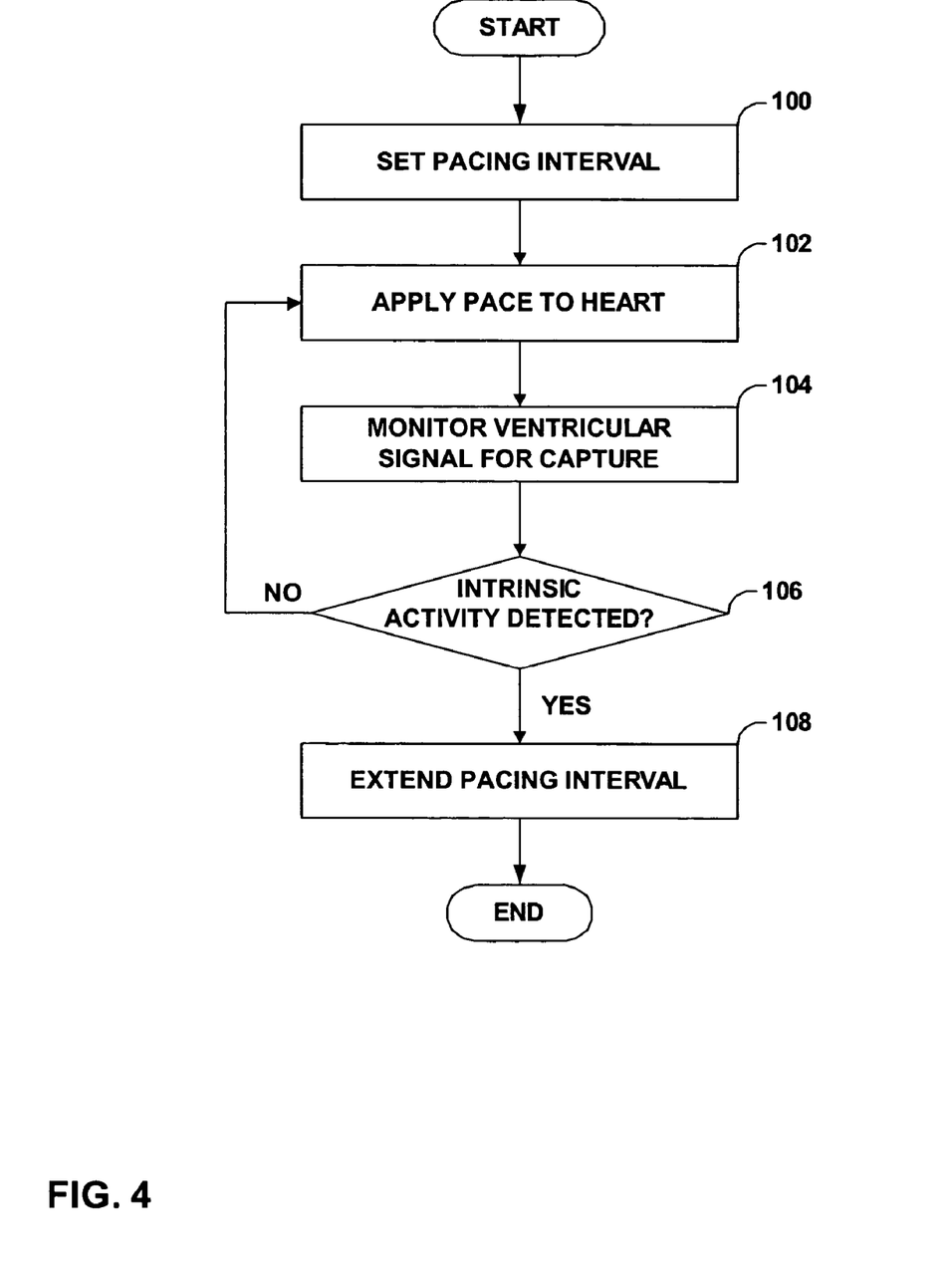
FIG. 4 is a flowchart illustrating an exemplary process to identify ventricular signals that contain possible intrinsic ventricular activity.

FIG. 4 is a flowchart illustrating an exemplary process to identify ventricular signals that contain intrinsic ventricular activity. As shown in FIG. 4, IMD 10 sets a pacing interval (100) such that IMD 10 delivers pacing pulses (102) separated by nearly constant intervals of time relative to previous time intervals. A lead positioned in a ventricle of a heart, such as lead 14, monitors signals within the ventricle for capture (104). Once, IMD 10 receives and processes the ventricular signal, IMD 10 can determine if intrinsic ventricular activity occurred within the ventricular signal (106) using one or more techniques mentioned above and described further below. Following the "NO" branch indicates that intrinsic ventricular activity was not detected within the ventricular signal. Thus, IMD 10 continues without extending the pacing interval. However, if IMD 10 detects intrinsic ventricular activity within the ventricular signal the "YES" branch is followed leading IMD 10 to extend the pacing interval by delaying delivery of a subsequent ventricular pacing pulse (108). If intrinsic ventricular activity occurs, IMD 10 inhibits the next pacing pulse and allows the intrinsic ventricular activity to proceed.

Figure 5:
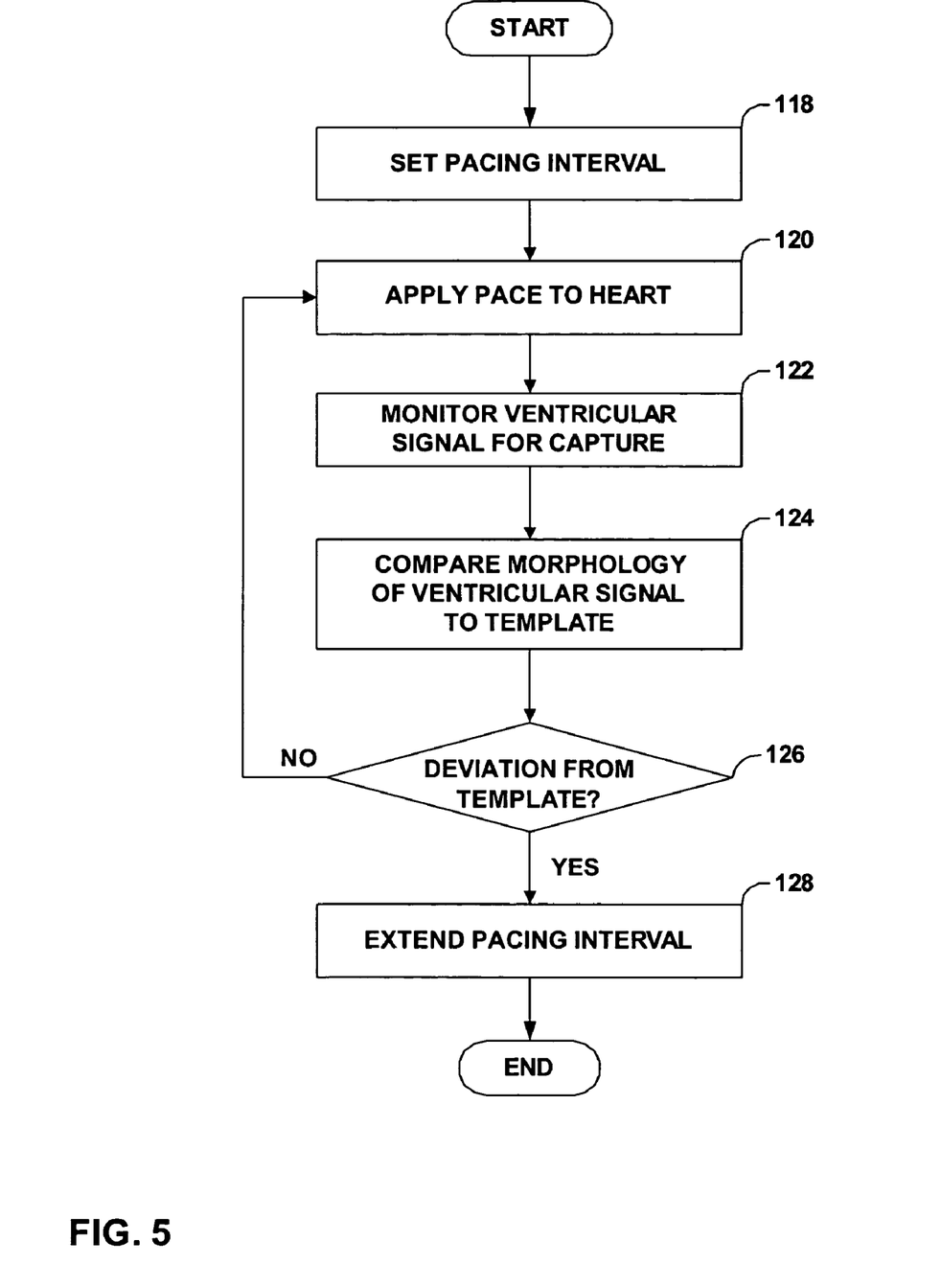
FIG. 5 is another flow chart illustrating a technique for identification of ventricular signals that contain possible intrinsic ventricular activity

FIG. 5 is another flow chart illustrating a technique for identification of ventricular signals that contain intrinsic ventricular activity. In particular, the technique compares morphological characteristics between a current ventricular signal and a template. Before IMD 10 performs the comparison a pacing interval is set (118) which determines the time interval between pacing pulses that are applied to a heart. A ventricular pacing pulse is delivered to a ventricle of the heart, such as ventricle 26 of heart 20 (120). IMD 10 then monitors ventricular signals via a lead inserted into a ventricle of the heart, such as lead 14 (FIG. 2). IMD 10 processes the signal as described above and compares the morphology of the ventricular signal to a template, or stored morphological criteria gathered from past ventricular signals in response to past ventricular pulses.

IMD 10 can generate a template during a training period (static templates) or dynamically while operating. The template generated during a training period comprises a template that represents morphological criteria of ventricular signals that fully capture a heart, such as heart 20 (FIG. 2). The criteria can be individually gathered for a particular patient during the training period to form a template unique to the patient. Templates generated dynamically during operation comprise morphological criteria from a single ventricular signal. Dynamic templates change during each beat and are continuously updated with new morphological criteria corresponding to the most recent ventricular signal. IMD 10 can use dynamic templates to perform "beat-to-beat" comparisons, where the template representing a most recent beat is compared to a subsequent beat or the current ventricular signal. Static and dynamic templates can be used alone or in conjunction to determine whether the current ventricular signal contains intrinsic ventricular activity.

By comparing a current ventricular signal to a template, IMD 10 can determine if a current ventricular signal exhibits morphology characteristics that deviate from the template (126). The template represents past ventricular signals in response to past ventricular pulses, and IMD 10 can compare one or more morphological characteristics of the current ventricular signal with the same one or more morphological characteristics of past ventricular signals represented by the template. In one embodiment, one or more morphological characteristics of the current signal need to deviate from the same morphological characteristics represented by the template enough to exceed a threshold. Once a predefined number of thresholds are exceeded, IMD 10 determines that the ventricular signal contains intrinsic ventricular activity ("YES" branch). If the predefined number of thresholds is not exceeded, IMD 10 continues to apply pacing pulses to the heart, without extending the pacing interval ("NO" branch).

The detection of intrinsic ventricular activity suggests that the ventricle of the heart is trying to contract autonomously. IMD 10 extends the pacing interval (128), allowing intrinsic ventricular activity to occur undisturbed. If the intrinsic ventricular activity does not occur during the extended pacing interval then IMD 10 delivers a ventricular pacing pulse to the ventricle. However, if the intrinsic ventricular activity does occur during the extended pacing interval, IMD 10 does not need to deliver a ventricular pace, which lengthens battery life, improves hemodynamic performance and increases patient comfort.

Figure 6:
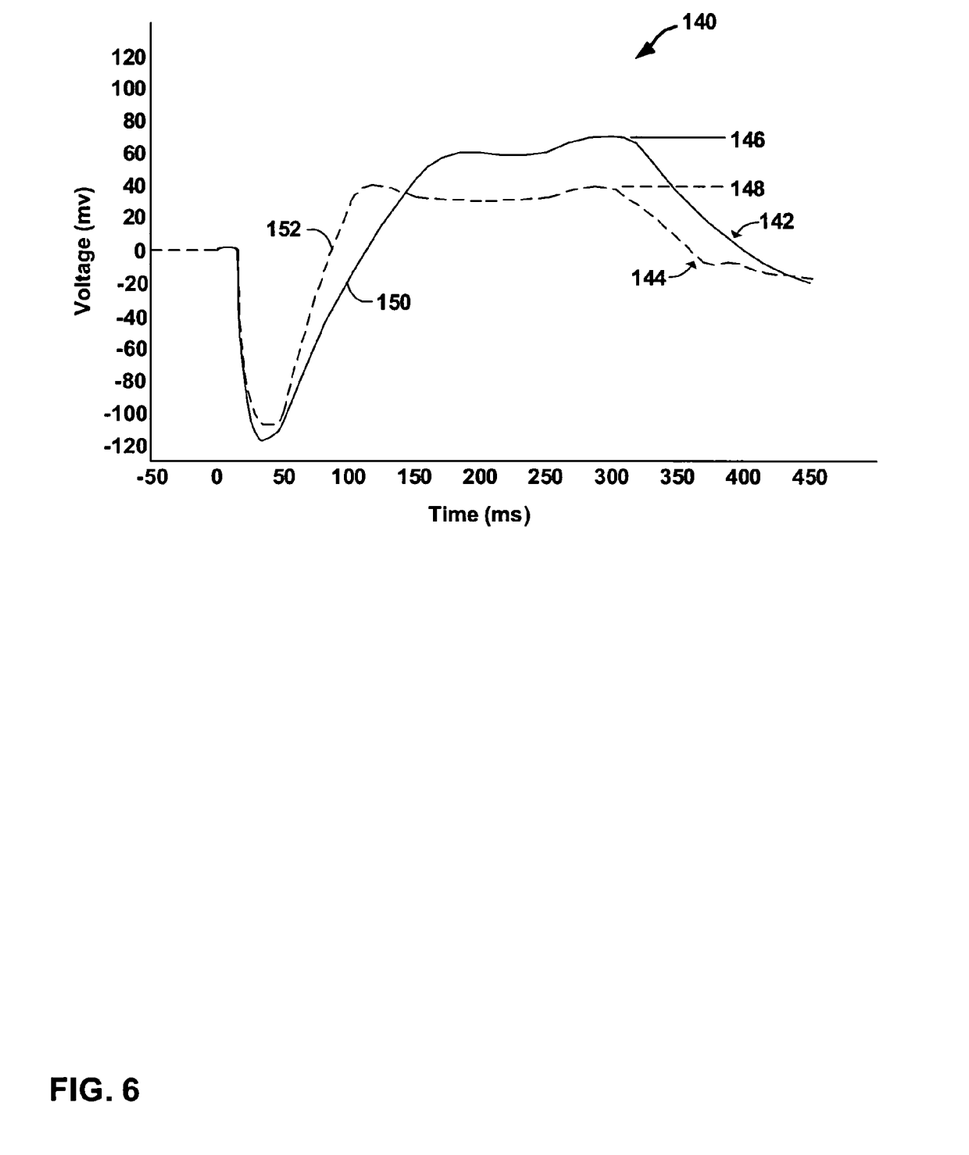
FIG. 6 is a graph illustrating a comparison between a morphology template and a current ventricular signal.

FIG. 6 is a graph illustrating a comparison between a static template and a current ventricular signal. It should be noted that the present invention could implement both static and dynamic templates. However, for exemplary purposes, only the static templates are referred to herein. The static template is represented by line 142, while the current ventricular signal is represented by line 144. Various morphological characteristics of the static template and the current ventricular signal are identified within their graphical representations. These morphological characteristics, as shown in FIG. 6, include a maximum amplitude 146 of line 142, a maximum amplitude 148 of line 144, a slope 150 of line 142 and a slope 152 of line 144. Both the template and the current ventricular signal, as well as their respective morphological characteristics are represented graphically to allow for visualization of certain principles of the invention. Templates and signals are stored in memory as a collection of discrete data points and need not be stored as graphs, such as graph 140.

The static template, as shown by line 142, represents a ventricular signal in response to a ventricular pacing pulse that fully captures a heart. Full capture is a term used to describe a pacing pulse that causes the heart to fully contract. A medical device, such as IMD 10 (FIG. 1), compares the template to current ventricular signals, which determines if the current ventricular signal fully captured the heart. In the example of FIG. 6, ventricular signals originate from both intrinsic ventricular activity and the given pace pulse, which has no full capture. The presence of intrinsic activity is made visible by comparing morphological characteristics associated with the ventricular signal containing no intrinsic ventricular activity, represented in graph 140 as line 144, to the static template represented by line 142.

Apparent morphological differences exist between lines 142 and 144. For example, maximum amplitude 146 of line 142 is elevated relative to maximum amplitude 148 of line 144. The difference between maximum amplitudes 146 and 148 can exceed a threshold which as a result can cause a medical device, such as IMD 10, to extend a pacing interval between a delivered pacing pulse and a subsequently delivered pacing pulse. A further example of a morphological difference between lines 142 and 144 exists when comparing slopes 150 and 152. As shown in graph 140, slope 150 of line 142 is smaller than slope 152 of line 144. This deviation from the template can suggest that the signal contains intrinsic ventricular activity, and that intrinsic ventricular activity is occurring within the heart. Further morphological characteristics that a medical device can use to determine intrinsic ventricular activity within a ventricular signal include a minimum amplitude of a signal, a width of a signal, T-wave timing and T-wave amplitude. One of more of these differences enables IMD 10 to detect the presence of intrinsic ventricular activity, and thereby distinguish between a full capture evoked response and a fusion evoked response.

Again, the medical device stores each of the above morphological characteristics, templates and signals as a collection of data points. The medical device can use pre-defined thresholds or can be trained to tailor unique thresholds corresponding to a particular patient. Thresholds are further stored as a collection of data points which can be dynamically altered in some cases to correspond to the particular patient. Other methods that use morphological characteristics but do not use thresholds can exist and are within the scope of the invention.

Figure 7:
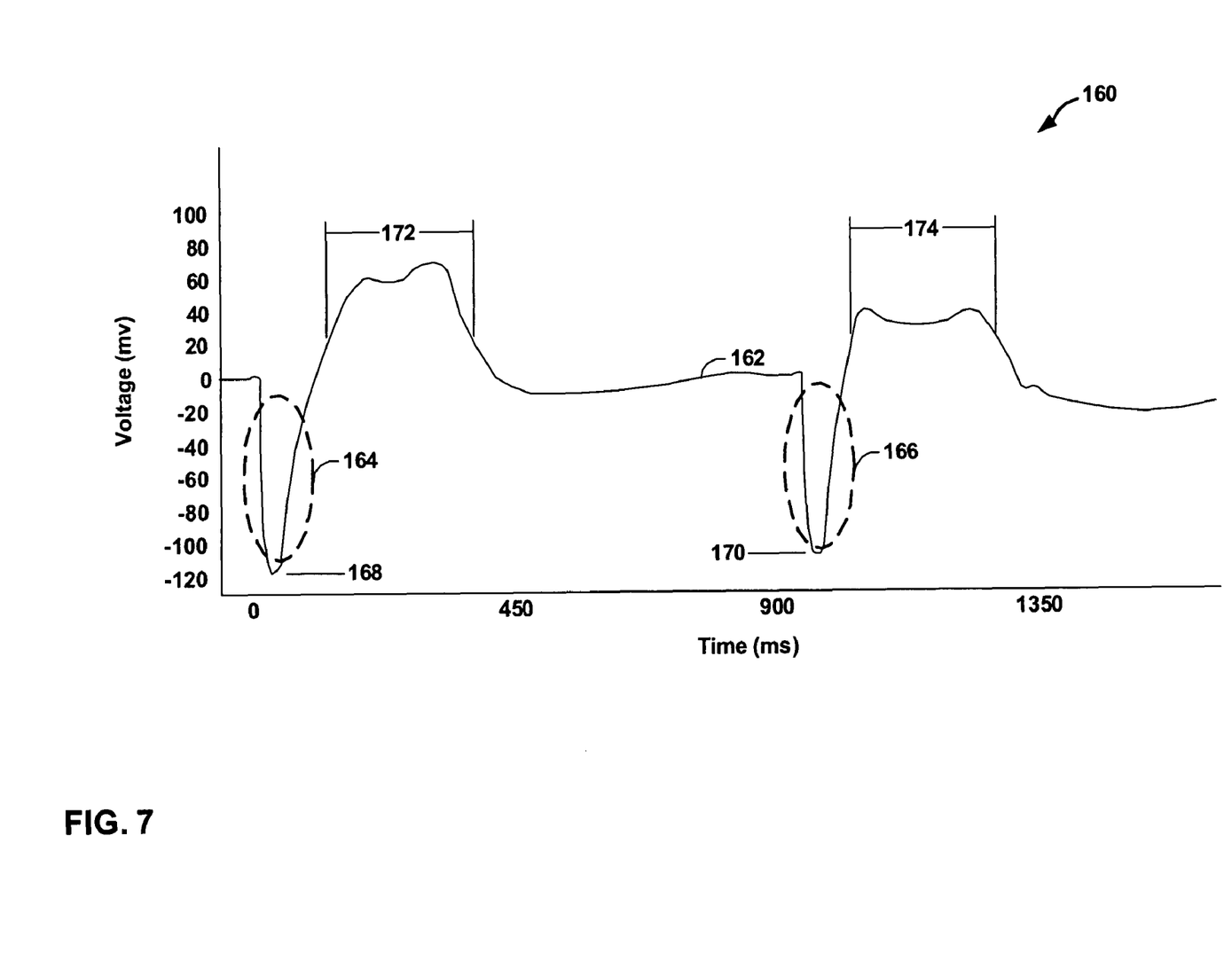
FIG. 7 is another graph illustrating a signal as measured by a sensing electrode from within a ventricle of a heart.

FIG. 7 is another graph illustrating a signal as measured by a pacing and sensing electrode from within a ventricle of a heart. A medical device, such as IMD 10 of FIG. 1, connected to the electrode, which can be similar to electrode 14, processes signal 162. The medical device begins processing signal 162 after each of depolarization 164 and 166 until the signal returns to near zero voltage levels.

Thus, signal 162 is broken into two ventricular signals. The medical device samples the first ventricular signal from 0 ms until approximately 450 ms and the second ventricular signal from approximately 930 ms until approximately 1350 ms. Both signals are processed by the medical device and morphological characteristics associated with each signal are measured.

The medical device can use the morphological characteristics of the first ventricular signal to update a dynamic template. The first signal is therefore the most recent ventricular signal. As follows, the second ventricular signal is the current ventricular signal. As discussed above, the medical device compares the morphological characteristics of the dynamic template to the current ventricular signal. If the current ventricular signal is within set thresholds then the medical device continues delivering pacing pulses separated by a nearly constant time interval. However, if the current ventricular signal deviates from the dynamic template then the medical device extends the pacing interval by delaying delivery of a subsequent pacing pulse.

Graph 160 depicts morphological characteristics of various types corresponding to the two ventricular signals apart of signal 162. The morphological characteristics include minimum amplitudes 168 and 170 as well as signal widths 172 and 174. The medical device can compare minimum amplitude 168 of the dynamic template to minimum amplitude 170 of the current ventricular signal. Minimum amplitudes 168 and 170 differ by approximately 5 millivolts. This mayor may not exceed a pre-defined threshold. Further comparisons of signal widths 172 and 174 by the medical device indicate that the current ventricular signal does not deviate much from the dynamic template. In this instance, the medical device compares two morphological characteristics, which indicate that the current ventricular signal does not contain intrinsic ventricular activity. Further comparisons using different morphological characteristics can yield a more accurate response and improve intrinsic ventricular activity identification accuracy.

Figure 8:
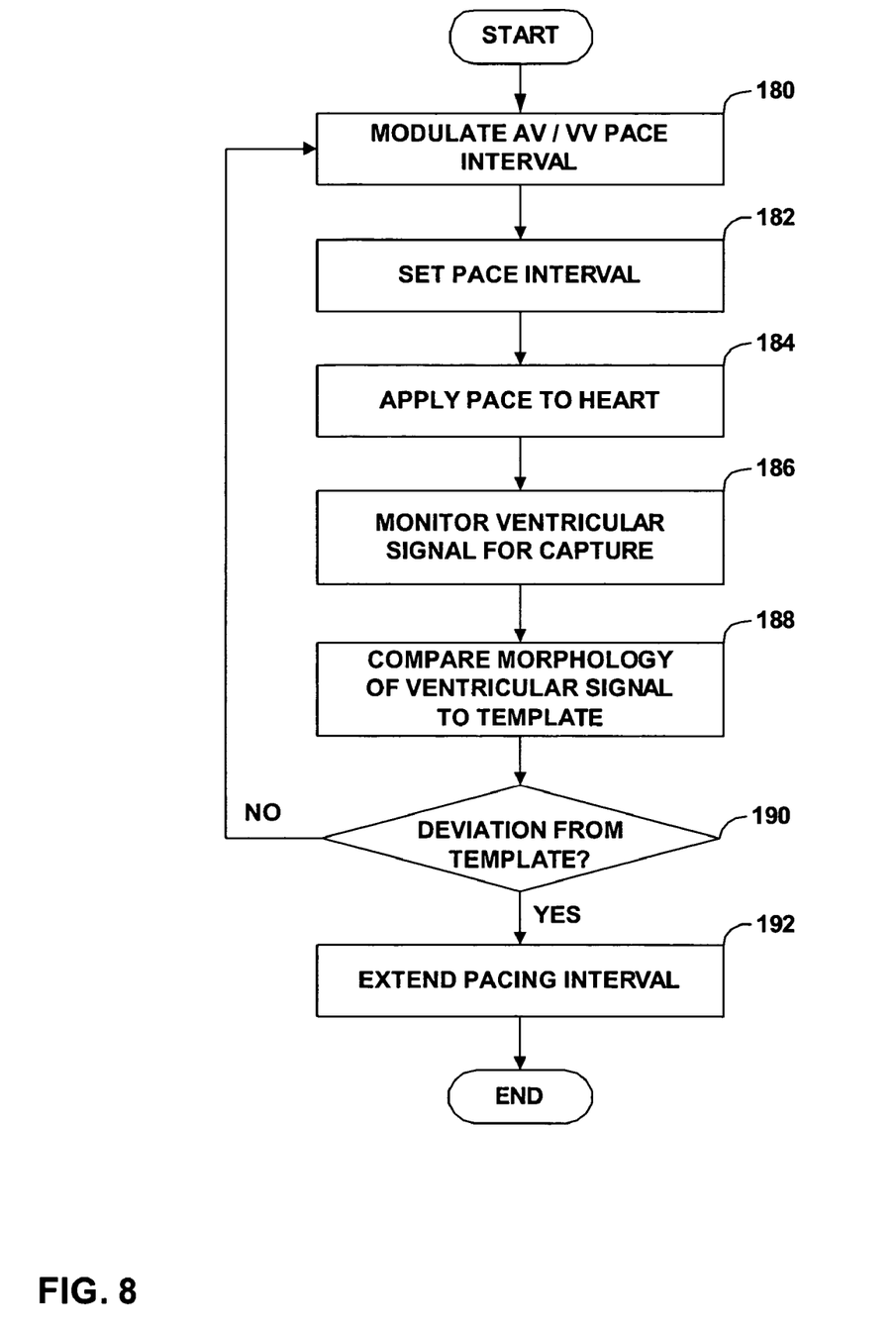
FIG. 8 is a flowchart illustrating another process to identify ventricular signals that contain possible intrinsic ventricular activity.

FIG. 8 is a flowchart illustrating another process to identify ventricular signals that contain intrinsic ventricular activity. In particular, a medical device, such as IMD 10 of FIG. 1, can slightly modulate a pacing interval by delivering a pacing pulse and subsequent pacing pulse separated by a time interval that the IMD slightly modulates. The time interval is typically referred to an atrial to ventricular (AN) time interval or ventricular to ventricular (VN) time interval. The medical device performs slight modulation of the AN or VN pacing interval to aid in determining whether a ventricular signal contains intrinsic ventricular activity. In other words, the modulation is used in an attempt to invoke a response that reveals intrinsic ventricular activity, while the intrinsic activity can be detected in a signal after the given pace pulse. The slight modulations can be achieved by randomly altering the delivery time of a pulse, following a pre-defined modulation scheme or allowing a user to specify the modulation scheme by specifying time interval tolerances and the like.

The medical device modulates the AN or VN pacing interval (180) and then sets the newly modulated pacing interval (182) such that paces are applied to a heart in a manner that reflects the newly modulated pacing interval (184). The medical device then monitors a ventricle of the heart, such as ventricle 26 of heart 20 (FIG. 2) via a medical lead placed in the ventricle and attached to the medical device. The medical device receives ventricular signals from the lead, which can be similar to lead 14, and monitors these signals for capture (186). As described above full capture is the goal of any pacing pulse.

The medical device further processes the signal and can use a variety of circuitry to analyze the ventricular signal gathering morphological characteristics. In some embodiments and as described above, the medical device can generate a static template during a training period and compare the template to the morphological characteristics of the ventricular signal (188). In other embodiments, the medical device can continuously update dynamic templates using morphological characteristics of a most recent ventricular signal. The dynamic template is then compared to the morphological characteristics of the current ventricular signal, providing a "beat-to-beat" comparison. A medical device can employ both of these techniques singly or in conjunction.

After the comparison of the template to the ventricular signal, the medical device can determine if the ventricular signal deviates from the template (190). If the ventricular signal is consistent with the template then the medical device returns to modulating the pacing interval to further determine if a subsequent ventricular signal contains intrinsic ventricular activity. However, if the ventricular signal does contain intrinsic ventricular activity, then the medical device extends the pacing interval by delaying delivery of a subsequent pacing pulse (192).

Many embodiments of the invention have been described. Various modifications can be made without departing from the scope of the claims. For example, the invention is not limited to the particular techniques described above for detecting intrinsic ventricular activity. Further techniques can combine techniques described above and use the techniques in conjunction to further increase accuracy of intrinsic ventricular activity detection. Also, the invention is not limited to the particular implantable medical devices described above, but can be practiced by a wide variety of implantable medical devices. For example, a single chamber implantable medical device can use the invention to identify intrinsic ventricular activity within ventricular signals. As a result the single chamber implantable medical device can lengthen battery life, improve hemodynamic flow of a heart and increase patient comfort.

In addition, the invention may be embodied as a computer-readable medium that includes instructions for causing a programmable processor to carry out the methods described above. A "computer-readable medium" includes but is not limited to read-only memory, Flash memory and a magnetic or optical storage medium. The instructions may be implemented as one or more software modules, which may be executed by themselves or in combination with other software.

These and other embodiments are within the scope of the following claims.

The invention claimed is:

1. A method comprising:
   delivering a ventricular pacing pulse to a heart;
   modulating a pacing interval at which the ventricular pacing pulse is delivered to aid in detecting whether an autonomous intrinsic signal component is present within the heart;
   sensing a ventricular signal response to the delivered pacing pulse;
   detecting whether an autonomous intrinsic signal component is present within the sensed ventricular signal response to the delivered pacing pulse; and
   extending the pacing interval between the delivered ventricular pacing pulse and a subsequently scheduled ventricular pacing pulse responsive to the autonomous intrinsic signal component being detected;
   wherein detecting whether an autonomous intrinsic signal component is present comprises: comparing a morphological characteristic of a past ventricular signal response to a past pacing pulse known to fully capture the heart to the same morphological characteristic of the sensed ventricular signal response to the delivered pacing pulse; and
   determining whether the ventricular signal response to the delivered pacing pulse originates from both autonomous intrinsic ventricular activity and the ventricular pacing pulse in response to the comparison of the morphological characteristics.

2. The method of claim 1, wherein modulating the pacing interval includes modulating an atrial to ventricular pacing delay.

3. The method of claim 1, wherein the subsequently delivered pacing pulse comprises a pacing pulse delivered to a ventricle of the heart after the delivered pacing pulse.

4. The method of claim 1, wherein detecting whether an autonomous intrinsic signal component is present within the heart comprises comparing a morphological characteristic of a past T-wave following a past pacing pulse known to fully capture the heart to the same morphological characteristic of a T-wave following the delivered pacing pulse.

5. The method of claim 1, wherein a past ventricular signal further comprises a most recent ventricular signal resulting from a most recent pacing pulse.

6. The method of claim 1, wherein the morphological characteristic includes at least one of a minimum amplitude of a signal, a maximum amplitude of a signal, a width of a signal, a slope of a signal, T-wave timing and T-wave amplitude.

7. A device comprising:
   at least one electrode to deliver a ventricular pacing pulse to a heart and sense a ventricular signal response to the delivered pacing pulse; and
   a processor that modulates a pacing interval at which the ventricular pacing pulse is delivered to aid in detecting whether an autonomous intrinsic signal component is present within the heart, detects whether an autonomous intrinsic signal component is present within the sensed ventricular response within the heart after delivering the ventricular pacing pulse and extends the pacing interval between the delivered pacing pulse and a subsequently scheduled pacing pulse responsive to the autonomous intrinsic signal component being detected,
   wherein detecting whether an autonomous intrinsic signal component is present comprises: comparing a morphological characteristic of a past ventricular signal response to a past pacing pulse known to fully capture the heart to the same morphological characteristic of the sensed ventricular signal response to the delivered pacing pulse; and
   determining the ventricular signal response to the delivered pacing pulse originates from both autonomous intrinsic ventricular activity and the ventricular pacing pulse in response to the comparison of the morphological characteristics.

8. The device of claim 7, wherein the processor modulates the pacing interval by modulation of an atrial to ventricular delay.

9. The device of claim 7, wherein the electrode comprises an electrode to deliver a pacing pulse to a ventricle of the heart.

10. The device of claim 7, wherein the processor detects whether an autonomous intrinsic signal component is present by comparing a morphological characteristic of a past T-wave following a past pacing pulse known to fully capture the heart to the same morphological characteristic of a T-wave following the delivered pacing pulse.

11. The device of claim 10, further comprising a memory to store the past ventricular signal.

12. The device of claim 7, wherein the processor compares a most recent ventricular signal resulting from a most recent pacing pulse to a ventricular signal resulting from a past pacing pulse known to fully capture the heart.

13. The device of claim 7, wherein morphological characteristic comprises at least one of a minimum amplitude of a signal, a maximum amplitude of a signal, a width of a signal, a slope of a signal, T-wave timing and T-wave amplitude.

14. A non-transitory computer-readable medium comprising instructions to cause a processor to:
   control a pulse generator to deliver a ventricular pacing pulse to a heart;

modulate a pacing interval at which the ventricular pacing pulse is delivered to aid in detecting whether an autonomous intrinsic signal component is present within the heart sense a ventricular signal response to the delivered ventricular pacing pulse;

detect whether an autonomous intrinsic signal component is present within the sensed ventricular signal response within the heart after delivering the pacing pulse; and extend the pacing interval between the delivered pacing pulse and a subsequently scheduled pacing pulse responsive to the autonomous intrinsic signal component being detected wherein detecting whether an autonomous intrinsic signal component is present comprises: comparing a morphological characteristic of a past ventricular signal response to a past pacing pulse known to fully capture the heart to the same morphological characteristic of the sensed ventricular signal response to the delivered pacing pulse; and determining whether the ventricular signal response to the delivered pacing pulse originates from both autonomous intrinsic ventricular activity and the ventricular pacing pulse in response to the comparison of the morphological characteristics.

15. The non-transitory computer-readable medium of claim 14, wherein the instructions cause the processor to modulate the pacing interval by modulation of an atrial to ventricular delay.

16. The non-transitory computer-readable medium of claim 14, wherein the subsequently delivered pacing pulse comprises a pacing pulse delivered to a ventricle of the heart after the delivered pacing pulse.

17. The non-transitory computer-readable medium of claim 14, wherein the instructions cause the processor to detect whether an autonomous intrinsic signal component is present within the heart by comparing a morphological characteristic of a past T-wave following a past pacing pulse known to fully capture the heart to the same morphological characteristic of a T-wave following the delivered pacing pulse.

18. The non-transitory computer-readable medium of claim 14, wherein the past ventricular signal further comprises a most recent ventricular signal resulting from a most recent pacing pulse.

19. The non-transitory computer-readable medium of claim 14, wherein the morphological characteristic includes a minimum amplitude of a signal, a maximum amplitude of a signal, a width of a signal, a slope of a signal, T-wave timing and T-wave amplitude.

20. A method comprising:

delivering a pacing pulse to a heart;

modulating a pacing interval by randomly altering a delivery time of the pacing pulse to aid in detecting whether an autonomous intrinsic signal component is present within the heart;

sensing a signal response to the delivered pacing pulse;

detecting whether an autonomous intrinsic signal component is present within the sensed signal response to the delivered pacing pulse; and extending the pacing interval between the delivered pacing pulse and a subsequently scheduled pacing pulse responsive to the autonomous intrinsic signal component being detected;

wherein detecting whether an autonomous intrinsic signal component is present comprises comparing a morphological characteristic of a past signal response to a past pacing pulse to the same morphological characteristic of the sensed signal response to the delivered pacing pulse.

* * * * *